US00PP32104P2

(12) United States Plant Patent
Hansen

(10) Patent No.: US PP32,104 P2
(45) Date of Patent: Aug. 18, 2020

(54) ***ECHINACEA* PLANT NAMED 'YELLOW MY DARLING'**

(50) Latin Name: ***Echinacea* hybrid**
Varietal Denomination: Yellow My Darling

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,732

(22) Filed: Nov. 26, 2019

(51) Int. Cl.
*A01H 6/14* (2018.01)
*A01H 5/02* (2018.01)

(52) U.S. Cl.
USPC ..... Plt./428

(58) Field of Classification Search
USPC ..... Plt./428
CPC ..... A01H 6/14; A01H 5/02
See application file for complete search history.

*Primary Examiner* — Annette H Para

(57) ABSTRACT

The new and distinct cultivar of *Echinacea* plant named 'Yellow My Darling', with fragrant inflorescences on strong stems having a single whorl of rich yellow ray florets with a light green center that lighten to creamy yellow. The new plant has oval to ovate dark-green foliage. The flowers from mid-summer to late summer, and is suitable as a potted plant, for the landscape, and for cut flower arrangements.

1 Drawing Sheet

Botanical denomination: *Echinacea* hybrid.
Cultivar designation: 'Yellow My Darling'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Dec. 1, 2018. *Echinacea* 'Yellow My Darling' was listed with a photograph and brief description in the "Walters Gardens 19-20 Catalog" distributed first on May 29, 2019. The claimed plant was first sold on Jul. 8, 2019 by Walters Gardens, Inc., who obtained the plant and all information relating thereto, from the inventor. No plants of *Echinacea* 'Yellow My Darling' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'Yellow My Darling'. The new plant was the result of a self-pollination by the inventor of an unnamed proprietary hybrid known as 14-3-11 (not patented) on Jul. 15, 2015 at a wholesale perennial nursery in Zeeland, Mich. This seedling was evaluated first in trials in the summer of 2016 at the same nursery and assigned the breeder code of 15-3-6. *Echinacea* 'Yellow My Darling' has been asexually propagated at the same nursery by crown division since 2017 and also using careful shoot tip tissue culture procedures and found to reproduce plants that exhibit all the characteristics identical to the original plant.

*Echinacea* 'Yellow My Darling' is distinct from all other Coneflowers known to the inventor. The nearest comparison cultivars are 'Matthew Saul' U.S. Pat. No. 17,652, 'Leilani' U.S. Plant Pat. No. 23,526, 'Maui Sunshine' U.S. Plant Pat. No. 22,808, 'Balsomemy' U.S. Plant Pat. No. 24,768, 'Balsomemyim' U.S. Plant Pat. No. 30,116, 'Canary Feathers' U.S. Plant Patent Application copending, 'Julia' U.S. Plant Pat. No. 24,629, 'Cleopatra' U.S. Plant Pat. No. 24,631 and 'TNECHKY' U.S. Plant Pat. No. 29,922.

The parent plant, 14-3-11, was not maintained as either plants or in photography, so no comparison is possible. 'Matthew Saul' is slightly shorter in habit and the ray florets are smaller and the coloration is not as deep bright yellow. 'Leilani' is slightly shorter in habit and ray florets have a more orange overlay. 'Maui Sunshine' is taller in habit and has ray florets that are less bright yellow. 'Balsomemy' produces slightly smaller plants, without branching stems, with smaller, fewer, more subtending and more narrow ray tepals that have a coloration that is more orangish-yellow. 'Balsomenmyim' is slightly smaller in habit and the inflorescences produce chaff or spines that are more orange and less dark red. 'Canary Feathers' has a lighter yellow ray florets. 'Julia' has orange ray florets that are less overlapping and more drooping. 'Cleopatra' has ray florets that are less overlapping and are lighter yellow. 'TNECHKIO' has much shorter habit and smaller ray tepals that are not as bright yellow.

SUMMARY OF THE INVENTION

*Echinacea* 'Yellow My Darling' has not been evaluated under all possible environmental conditions. The phenotype may vary with variations in environment including: growing temperature, available sunlight, nutrients, water, etc. without a change in the genotype of the plant. The new plant is distinct from its parents and all other *Echinacea* known to the applicant in the following combined traits:

1. Fragrant inflorescences on strong branched stems;
2. Large, broad inflorescences with single whorl of ray florets that tend to stay horizontal once open;

3. Ray florets of rich yellow, with light green near the center, lighten to creamy yellow;
4. Vigorous growth and excellent habit;
5. Dark-green oval to ovate foliage.

BRIEF DESCRIPTION OF THE DRAWINGS

The photographs of the new plant demonstrate the overall appearance of the plant including the unique traits. The drawings of the new plant are of a two-year-old plant grown in full-sun trial garden in Zeeland, Mich. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
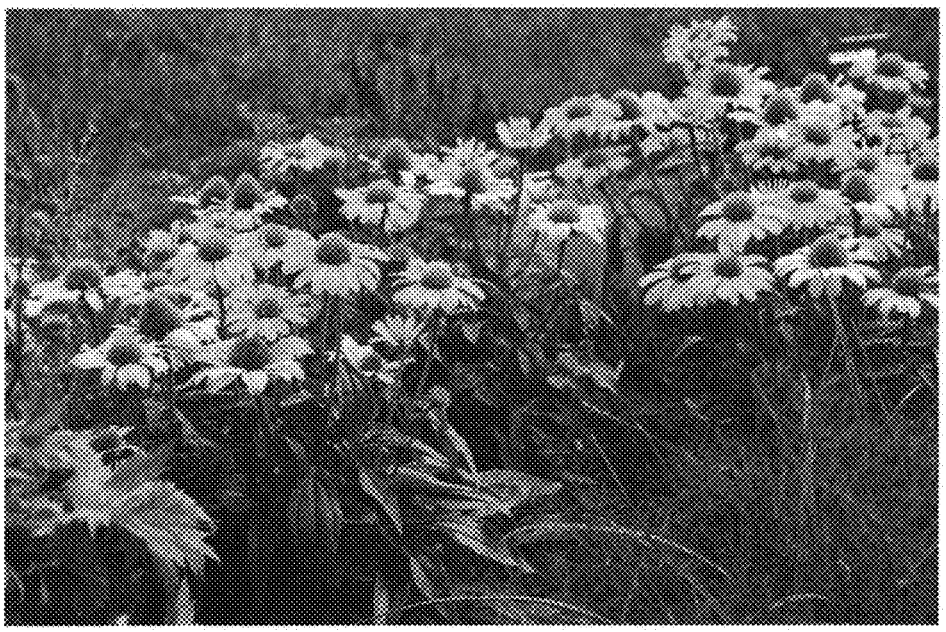
FIG. 1 shows the habit of the new plant in flower.
Figure 2:
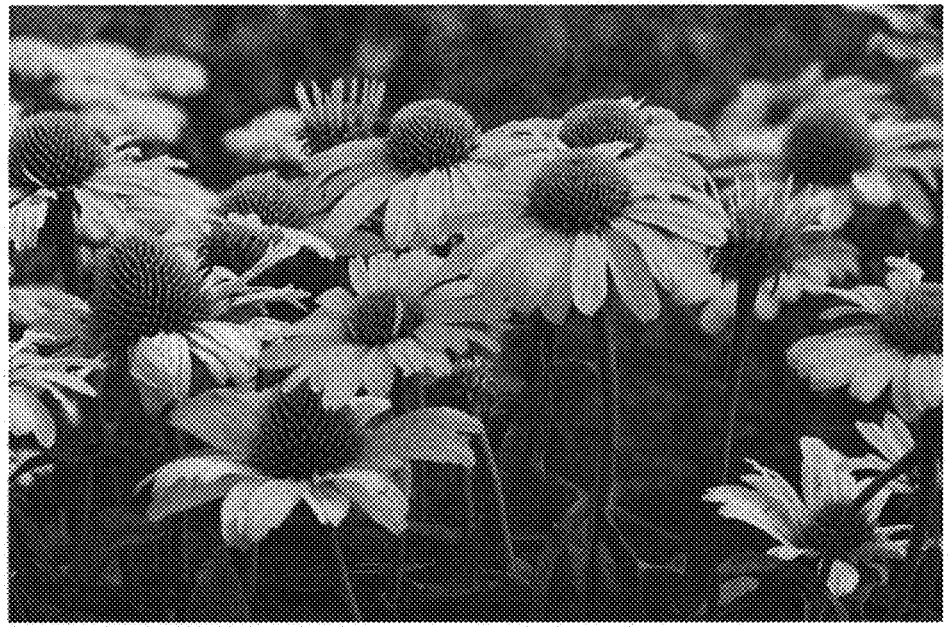
FIG. 2 shows a close up of some inflorescences of the new plant.

The following description of *Echinacea* 'Yellow My Darling' is based on observations of two-year-old specimens grown in a full-sun trial garden with supplemental water and fertilizer in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female and male parent is the proprietary unreleased hybrid 14-3-11;

Plant habit: Multi-stemmed, freely-branched, hardy herbaceous perennial, flowering to about 55.5 cm tall and foliage to 27 cm tall and 56 cm wide;

Growth rate: Vigorous, finishing in 4 liter containers in about 2 months during the summer;

Roots: Cream-colored, finely branched;

Foliage: Alternate; ovate; acute apex; attenuate base; margin dentate, micro-ciliolate; micro-strigillose abaxial and adaxial; to about 16.5 cm long and 7.0 cm wide decreasing distally, average about 12.5 cm long and 5.5 cm wide;

Leaf color: Young leaves adaxial nearest RHS 137B, abaxial nearest RHS 138A; mature leaves adaxial nearest NN137A, abaxial between RHS 147C and RHS 138A;

Foliage fragrance: Lightly herbal;

Venation: Pinnate; with two major arcuate veins on both sides of the midrib; abaxial midrib and veins costate; glabrate to glabrous adaxial, strigillose abaxial;

Vein color: Adaxial primary veins between RHS 145A and RHS N144A, secondary nearest RHS 137A; abaxial primary veins between RHS 145B and RHS 146D, secondary nearest RHS NN137A;

Petiole: Concavo-convex, strigillose adaxial and sparsely puberulent to strigillose abaxial; about 14.5 cm long and 8.0 mm wide on lowest leaves and decreasing to sessile distally; color nearest RHS 146D adaxial and abaxial nearest RHS 146D;

Peduncle: About 13 per plant; strigillose; cylindrical; strong stiff; upright; branched; average 24.0 cm long and 9.0 mm diameter; flowering in upper 36 cm;

Peduncle color: Between RHS 145A and RHS 145B;

Branches: Cylindrical; strigillose, tightly angled to main stem, to 60° to 75° above horizontal; to 23.0 cm long and 3.5 mm diameter; color between RHS 145A and RHS 145B;

Inflorescence: Bracteate head, aggregate of achene; with single whorl of distinct ligulate ray florets and disk florets in a pappus; flowering mid-summer to late summer; initial inflorescences largest, to about 90.0 mm across, average about 86.0 mm diameter with cones 4.0 cm across and 4.5 cm tall; approximately 4 inflorescences per peduncle;

Inflorescence fragrance: Lightly sweet;

Flower persistence: Remaining affective in color for 10 to 14 days depending on temperatures, cone drying on plant and effective into winter;

Involucre: With numerous bracts, about 48 per inflorescence in 4 whorls; arcuate downward toward peduncle;

Involucre bracts: Linear to lanceolate ; narrowly acute apex; truncate base; micro-ciliolate margin; adaxial glabrous; abaxial strigillose; average about 6.5 mm long and 3.5 mm across; color adaxial nearest RHS 138A, abaxial nearest RHS 137B;

Inflorescence buds with ray florets vertical and still enrolled: About 3.0 mm across and 25.0 mm tall; ray floret color RHS 10C with spines nearest RHS N144A;

Ray florets: Zygomorphic; agynic; astemonous; arrangement in single whorl, typically imbricate; lanceolate to spatulate; apex rounded, emarginated with two notches 0.5 to 1.5 mm deep; base cuneate; margin entire; adaxial and abaxial matte; abaxial base puberulent with pappus; 20 to 28 per inflorescence; opening to horizontal, drooping up to only 10° to 15° below horizontal with maturity; ligule to 50.0 mm long and 16.0 mm wide, average size 47.0 mm long, 14.5 mm wide at center tapering to 2 mm wide at base; thickened veins slightly raised;

Ray ligule color: Adaxial claw base nearest RHS 137A, next proximal 4 mm nearest RHS 145B, distal blade nearest RHS 14A; abaxial claw base nearest RHS 137A, blade center between RHS 10D and RHS 11D and margin nearest RHS 10C; before dropping adaxial blade base nearest RHS 145C, distally nearest RHS 11C and claw RHS 137A, abaxial blade between RHS 11C and RHS 11D and claw nearest RHS 137A;

Disc florets: About 300 to 400 per head; actinomorphic; perfect; synandrous; produced in raised dome, about 4.5 cm across and 4.0 cm tall; arranged in Fibonacci spiral;

Corolla: Fused forming tube; outer florets about 8.0 mm long and 2.0 mm wide, central florets about 9.0 mm long and 2.0 mm wide, tepals fused in basal 8.0 mm, free in distal 1.0 mm; individual tepals about 1.0 mm wide at fusion; acute apex; entire margin; surfaces slightly lustrous;

Corolla tube color: Adaxial and abaxial nearest RHS 144A except nearest RHS 145C in basal 1.0 mm;

Disk floret androecium: Five, synandrous;

Staminal column: About 0.7 mm wide and protrudes from corolla tube about 2 mm; five fused stamens;

Anthers: Fused, about 4.0 mm long and 0.7 mm diameter; color nearest RHS 202A;

Filaments: Five; attached to column; thin, less than 0.2 mm diameter and 0.5 mm long; color nearest RHS 158D;

Pollen: Globose, less 0.1 mm in diameter, RHS 17B;

Gynoecium: Single; to 9.0 mm long;

Style: About 6.5 mm long and 0.2 mm diameter; color between RHS 150D and RHS 145D;

Stigma: Bifid; about 2.0 mm long and 0.3 mm diameter; color nearest RHS 154D;

Fruit: Achene; pyramidal; about 4.5 mm long and 2.5 mm wide; acute base and fringed flattened apex; color variable nearest RHS 199D and between RHS 202A and RHS 202B;

Receptacle spines: With disk florets; acicular; to 14 mm long and 2.0 mm across;

Spine color: Upon opening apices nearest RHS 17B with bases nearest RHS 144A; mature flower apices nearest RHS N25D, and base nearest RHS N144D; after ray ligules fall apices nearest RHS N163D with base nearest RHS 145D; after dried nearest blend between RHS 200A and RHS 202A;

Disease resistance: Resistance beyond that of other hardy Coneflower cultivars has not been observed. The plant grows best with plenty of moisture and adequate drainage, but is able to tolerate some drought when mature. Hardiness at least from USDA zone 4 through 8.

I claim:

1. A new and distinct cultivar of *Echinacea* plant named 'Yellow My Darling' as herein described and illustrated.

* * * * *